United States Patent
Tazawa

(10) Patent No.: US 12,357,503 B2
(45) Date of Patent: Jul. 15, 2025

(54) OPHTHALMIC SURGICAL INSTRUMENT

(71) Applicant: MANI, INC., Tochigi (JP)

(72) Inventor: Yoshiyuki Tazawa, Tochigi (JP)

(73) Assignee: MANI, INC., Tochigi (JP)

( * ) Notice: Subject to any disclaimer, the term of this patent is extended or adjusted under 35 U.S.C. 154(b) by 758 days.

(21) Appl. No.: 17/276,224

(22) PCT Filed: Sep. 19, 2019

(86) PCT No.: PCT/JP2019/036676
§ 371 (c)(1),
(2) Date: Mar. 15, 2021

(87) PCT Pub. No.: WO2020/059773
PCT Pub. Date: Mar. 26, 2020

(65) Prior Publication Data
US 2022/0031509 A1      Feb. 3, 2022

(30) Foreign Application Priority Data

Sep. 21, 2018    (JP) ................................. 2018-177627

(51) Int. Cl.
*A61F 9/007* (2006.01)
*A61B 17/29* (2006.01)

(52) U.S. Cl.
CPC ...... *A61F 9/00736* (2013.01); *A61B 17/2909* (2013.01)

(58) Field of Classification Search
CPC ............. A61F 9/00736; A61B 17/2909; A61B 2017/305; A61B 17/30
See application file for complete search history.

(56) References Cited

U.S. PATENT DOCUMENTS

| | | |
|---|---|---|
| 2008/0195135 A1 | 8/2008 | Attinger |
| 2010/0160851 A1* | 6/2010 | Dimalanta .......... A61F 9/00736 604/22 |

(Continued)

FOREIGN PATENT DOCUMENTS

| | | | |
|---|---|---|---|
| JP | 2008-194465 A | 8/2008 | |
| WO | WO-2010064670 A1 * | 6/2010 | ......... A61F 9/00736 |
| WO | 2010-126076 A1 | 11/2010 | |

OTHER PUBLICATIONS

International Search Report dated Dec. 3, 2019 Issued in Patent Application No. PCT/JP2019/036676.

*Primary Examiner* — Phong Son H Dang
(74) *Attorney, Agent, or Firm* — RANKIN, HILL & CLARK LLP

(57) ABSTRACT

Provided is an ophthalmic surgical instrument which can prevent curving of a pipe during a surgical procedure and can pull out a reinforcement sleeve by a required length such that the reinforcement sleeve covers the pipe. An ophthalmic surgical instrument (10) working in an eyeball includes a body portion (15) having a through-hole, a reinforcement sleeve (13) contacting an inner surface of the through-hole of the body portion (15), a pipe (12) passing through the inside of the reinforcement sleeve (13) and having a working portion (11) protruding from a tip end, and a movement member (17) connected to the pipe (12) and sliding in an axial direction of the ophthalmic surgical instrument to slide the pipe (12). A first slide mechanism allowing the reinforcement sleeve (13) to slide in the axial direction of the ophthalmic surgical instrument and a second slide mechanism allowing the pipe (12) to slide in the axial direction of the vitreous forceps are provided. Any one of the first and second slide mechanisms is an independent slide mechanism not influenced by the other slide mechanism.

5 Claims, 3 Drawing Sheets

(56) References Cited

U.S. PATENT DOCUMENTS

2014/0128896 A1* 5/2014 Ryan .................. A61F 9/00736
  606/170
2016/0022256 A1 1/2016 Peterson

* cited by examiner (a)

(b)

(a)

(b)

OPHTHALMIC SURGICAL INSTRUMENT

TECHNICAL FIELD

The present invention relates to an ophthalmic surgical instrument used for a vitreous surgery, such as vitreous forceps.

BACKGROUND ART

A vitreous surgery is an ophthalmic surgery for cutting/removing a jellylike vitreous body in an eyeball or a proliferative membrane formed on a retina due to deformation of a vitreous body. In such a vitreous surgery, when, e.g., an ophthalmic surgical instrument is used in the eyeball, a cannula is first attached to the eyeball, and, e.g., the ophthalmic surgical instrument is inserted through the cannula (see, e.g., Patent Literature 1). Note that examples of the ophthalmic surgical instrument include vitreous forceps for holding and removing the vitreous body.

FIG. 5 illustrates views upon use of typical vitreous forceps, FIG. 5(a) illustrating the state of a process on a far side of an eyeball and FIG. 5(b) illustrating the state of a process on a near side of the eyeball. It is configured such that a general cannula 20 attached to the eyeball E in a vitreous surgery is, in the vicinity of a base end portion of a metal pipe, fitted in a resin base.

The vitreous forceps 100 are configured such that a working portion 101 for holding a vitreous body is provided at a tip end of the pipe 102 protruding from a body portion 105. The pipe 102 is inserted into the eyeball E through the cannula 20, and therefore, an extremely-thin material is used.

In a case where the process of holding the vitreous body at a portion deep in the eyeball E is performed as in FIG. 5(a), the length of the pipe 102 extending out of the cannula 20 is short, and therefore, there is almost no probability that the pipe 102 is curved even when the body portion 105 is moved. However, in a case where the process of holding the vitreous body on the near side of the eyeball E as in FIG. 5(b), the length of the pipe 102 extending out of the cannula 20 is long, and therefore, there is a probability that the pipe 102 is curved as in the figure when the body portion 105 is moved. For this reason, there is a surgical probe configured so that for reducing curving of the pipe 102, the pipe 102 can be covered with a reinforcement sleeve (see, e.g., Patent Literature 2).

FIG. 6 illustrates a cross-sectional view of the typical surgical probe having the reinforcement sleeve. The reinforcement sleeve 103 provided at the probe (the vitreous forceps) 100 disclosed in Patent Literature 2 is biased to an eyeball side (a cannula 20 side) by a spring 110, and during a surgical procedure, is constantly in a state in which the reinforcement sleeve 103 contacts the cannula 20. That is, the pipe 102 positioned outside the cannula 20 is basically always in a state in which the pipe 102 is reinforced by the reinforcement sleeve 103.

However, in the case of the vitreous forceps with such a configuration, the eyeball is constantly kept pressed under action of biasing force of the spring 110. This provides a burden on the eyeball, and constantly provides reactive force of the spring 110 to a practitioner through the held body portion 105. Such a state is not preferred because interference with a fine process is caused.

CITATION LIST

Patent Literature

PATENT LITERATURE 1: WO 2010/126076 A
PATENT LITERATURE 2: JP-A-2008-194465

SUMMARY OF INVENTION

Problems to be Solved by Invention

In view of the above-described situation, the present invention is intended to provide an ophthalmic surgical instrument configured so that curving of a pipe of, e.g., vitreous forceps can be prevented during a surgery and a pipe can be covered with a required length of a reinforcement sleeve.

Solution to Problems

An ophthalmic surgical instrument according to the present invention is an ophthalmic surgical instrument working in an eyeball, including: a body portion including a through-hole; a reinforcement sleeve contacting an inner surface of the through-hole of the body portion; a pipe passing through an inside of the reinforcement sleeve and having a working portion protruding from a tip end; and a movement member connected to the pipe and sliding in an axial direction of the ophthalmic surgical instrument to slide the pipe. A first slide mechanism allowing the reinforcement sleeve to slide in the axial direction of the ophthalmic surgical instrument and a second slide mechanism allowing the pipe to slide in the axial direction of the ophthalmic surgical instrument are provided, and any one of the first and second slide mechanisms is an independent slide mechanism not influenced by the other slide mechanism.

The movement member may be connected to the pipe on a base side of the ophthalmic surgical instrument, or the reinforcement sleeve may include a slit in the axial direction. Moreover, the reinforcement sleeve may include a claw portion at a back end position, and the claw portion may contact the inside of the body portion. Further, a metal tip end reinforcement pipe may be provided on a tip end side of the reinforcement sleeve, and the pipe may penetrate the tip end reinforcement pipe.

Effects of Invention

According to the present invention, there are advantageous effects that the reinforcement sleeve slidably covers the pipe so that curving of the pipe can be prevented and moderately contacts the body portion of the ophthalmic surgical instrument so that the reinforcement sleeve can receive friction resistance upon sliding and can cover the pipe by a required length. Moreover, the reinforcement sleeve and the pipe form the mechanisms sliding independently of each other, and therefore, there is an advantageous effect that the degree of freedom in design of other slide mechanisms can be improved.

The movement member is connected to the pipe on the base side of the ophthalmic surgical instrument, and therefore, there is an advantageous effect that there is no necessity of limiting a configuration such as the length of the reinforcement sleeve.

The reinforcement sleeve includes a slit in the axial direction such that the outer diameter of the reinforcement sleeve is slightly elastically deformable and proper friction force is selectable. Moreover, the slit of the reinforcement sleeve fulfills a role as a clearance portion upon sliding of the pipe, and therefore, there is an advantageous effect that independent sliding can be reliably made without these components following each other.

DESCRIPTION OF EMBODIMENTS

Hereinafter, an embodiment of the present invention will be described with reference to the attached drawings.

Figure 1:
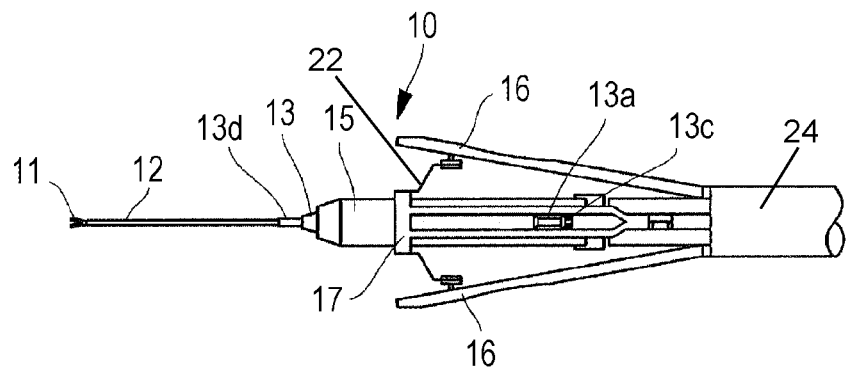
FIG. 1 illustrates an ophthalmic surgical instrument of the present invention, FIG. 1(a) illustrating a state in which a reinforcement sleeve is pulled in and FIG. 1(b) illustrating a state in which the reinforcement sleeve is pulled out.
Figure 1:
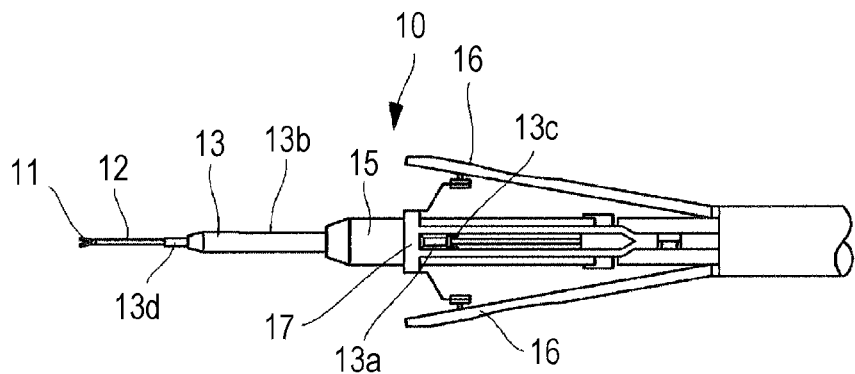
Figure 2:
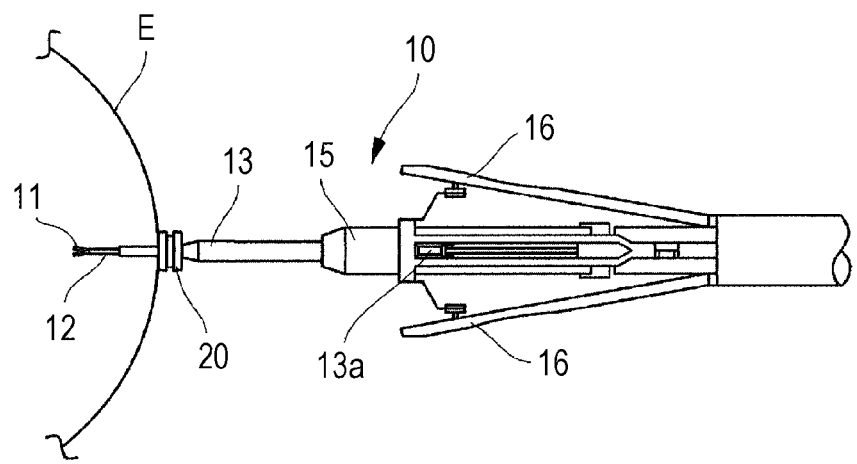
FIG. 2 illustrates a view upon use of the ophthalmic surgical instrument of the present invention.

FIG. 1 illustrates an ophthalmic surgical instrument of the present invention, FIG. 1(a) illustrating a state in which a reinforcement sleeve is pulled in and FIG. 1(b) illustrating a state in which the reinforcement sleeve is pulled out. Moreover, FIG. 2 illustrates a view upon use of the ophthalmic surgical instrument of the present invention. Note that vitreous forceps will be specifically described as the ophthalmic surgical instrument 10. However, a main portion of the present invention is a slide mechanism, and therefore, the present invention is also applicable to ophthalmic surgical instruments other than the vitreous forceps.

Basic operation of the ophthalmic surgical instrument 10 is that a forceps portion of a working portion 11 at a tip end of the ophthalmic surgical instrument 10 is closed when operating portions 16 are closed with fingers and is opened when the operating portions 16 are opened. The working portion 11 includes the forceps portion protruding from a tip end of a pipe 12 and a shaft portion passing through the inside of the pipe 12, and is fixed in the vicinity of bases of the operating portions 16. A structure is made such that the process of opening/closing the working portion 11 is performed in such a manner that by pressing or releasing of the operating portions 16, a movement member 17 connected to the operating portions 16 through plate springs 22 moves in an axial direction relative to a body portion 15 and the pipe 12 connected to the movement member 17 further moves in the axial direction (a second slide mechanism).

A basic configuration of the ophthalmic surgical instrument 10 has the pipe 12 outside the shaft portion of the working portion 11, a reinforcement sleeve 13 outside the pipe 12, the body portion 15 outside the reinforcement sleeve 13, and the movement member 17 outside the body portion 15. The movement member 17 and the pipe 12 described herein may be connected to each other on a base 24 side of the ophthalmic surgical instrument 10. With this configuration, one of sliding (a first slide mechanism) of the reinforcement sleeve 13 or sliding (the second slide mechanism) of the pipe 12 is independently performed without influence of the other sliding, and at the same time, the degree of freedom in design of other slide mechanisms is improved.

The pipe 12 is inserted into an eyeball E through a cannula 20, and therefore, an extremely-thin material such as 27 gauge is used. Thus, curving of the pipe 12 outside the cannula 20 needs to be prevented. For this reason, it is configured such that the reinforcement sleeve 13 covers the pipe 12 to reduce curving of the pipe 12. The reinforcement sleeve 13 is a member penetrating a through-hole of the body portion 15 and configured slidably in contact with an inner surface of the through-hole.

Figure 3:
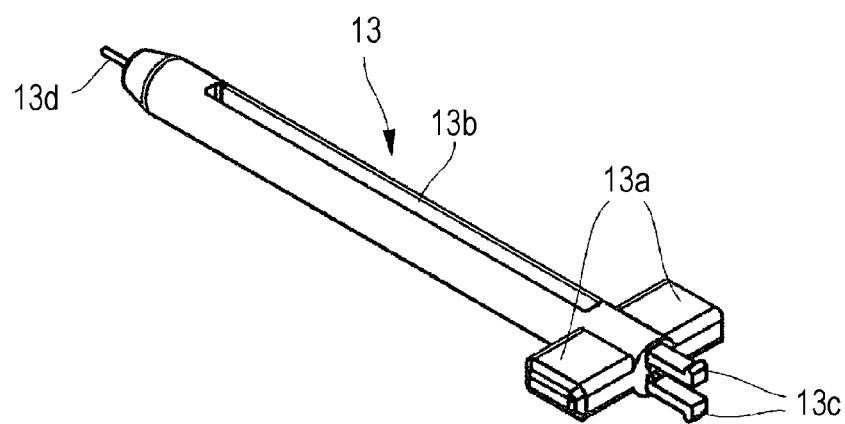
FIG. 3 illustrates a perspective view of the reinforcement sleeve.

FIG. 3 illustrates a perspective view of the reinforcement sleeve. A body portion of the reinforcement sleeve 13 is basically made of resin, and is configured so that the pipe 12 can penetrate the reinforcement sleeve 13 in the axial direction. The reinforcement sleeve 13 has such a structure (the first slide mechanism) that the reinforcement sleeve 13 can slide in the axial direction relative to the body portion 15 and the pipe 12 while fingers are contacting slide knobs 13a. The reinforcement sleeve 13 described herein is attached through the through-hole of the body portion 15. However, if friction with the through-hole is too high, it is difficult to slide the reinforcement sleeve 13. Conversely, if the friction is too low, the reinforcement sleeve 13 moves on its own during a surgery, and it is difficult to perform a surgical procedure.

For these reasons, the reinforcement sleeve 13 and the body portion 15 need to be attached such that moderate friction acts between the reinforcement sleeve 13 and the body portion 15. However, due to a manufacturing error, it is difficult to adjust friction force between the reinforcement sleeve 13 and the body portion 15 to a proper value only by size control. For this reason, a slit 13b is provided at the reinforcement sleeve 13, and therefore, a structure in which the outer diameter of the reinforcement sleeve 13 can be slightly elastically deformed is made. Since elastic deformation is allowed, the reinforcement sleeve 13 can penetrate the through-hole of the body portion 15 even if the reinforcement sleeve 13 is manufactured slightly thick and can slide while receiving proper friction. In a case where no slit 13b is formed at the reinforcement sleeve 13, even if the pipe 12 has slight distortion, there is a probability that when the pipe 12 slides in the axial direction, the reinforcement sleeve 13 follows the pipe 12 and slides together with the pipe 12. However, the slit 13b fulfills a role as a clearance portion for the pipe 12, and therefore, there is no probability that the reinforcement sleeve 13 follows the pipe 12. That is, sliding (the second slide mechanism) of the pipe 12 and sliding (the first slide mechanism) of the reinforcement sleeve 13 can be reliably independently performed. Note that the depth of the slit 13b may be about the half of the diameter of the reinforcement sleeve 13.

For a process on a far side of the eyeball E, the reinforcement sleeve 13 may be pulled into the body portion 15 as in FIG. 1(a). For a process on a near side of the eyeball E, the reinforcement sleeve 13 may be pulled out as in FIG. 1(b), and may be used with the reinforcement sleeve 13 covering the pipe 12. At this point, proper friction force acts on the reinforcement sleeve 13 and the body portion 15 as described above, and therefore, a state in which the reinforcement sleeve 13 is pulled out by a required length can be maintained and the reinforcement sleeve 13 can be easily slid with the slide knobs 13a being held. Thus, a pull-out amount is easily changed.

Claw portions 13c may be provided at a back end of the reinforcement sleeve 13. As long as the claw portion 13c also has an elastically-deformable structure and provides pressing force to, e.g., an inner surface of the body portion 15 with such force that the reinforcement sleeve 13 can slide, the shape of the claw portion 13c is not specifically limited. With these claw portions 13c, the reinforcement sleeve 13 can cover an optional length of the pipe 12, and such a state can be maintained.

A tip end reinforcement pipe 13d may be provided on a tip end side of the reinforcement sleeve 13. That is, it is configured such that the body portion of the reinforcement sleeve 13, the tip end reinforcement pipe 13d, and the pipe 12 have the same axis and the pipe 12 penetrates holes of the reinforcement sleeve 13 and the tip end reinforcement pipe 13d. The tip end reinforcement pipe 13d is made of metal so that contact with the pipe 12 passing through the hole of the tip end reinforcement pipe 13d can be accurately and smoothly made and rattling of the reinforcement sleeve 13 and the pipe 12 can be reduced.

Figure 4:
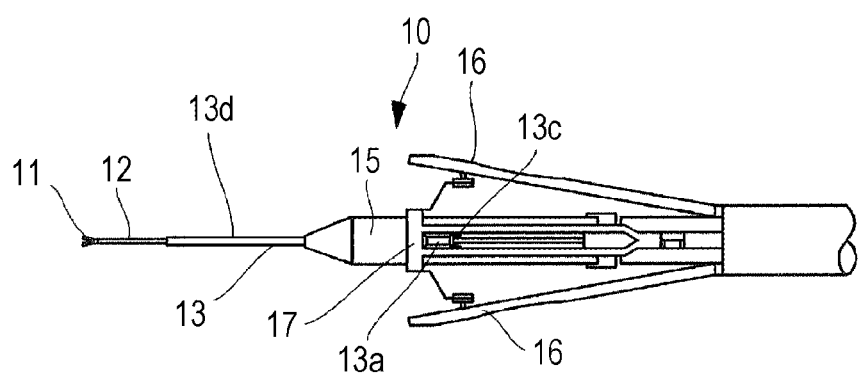
FIG. 4 illustrates an example in a case where a tip end reinforcement pipe is long.
Figure 5:
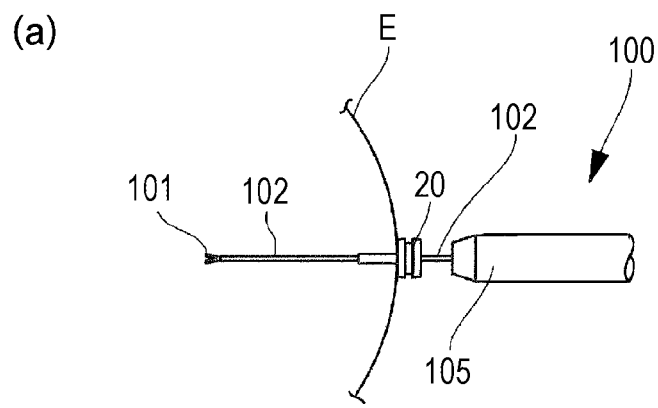
FIG. 5 illustrates views upon use of typical vitreous forceps, FIG. 5(a) illustrating the state of a process on a far side of an eyeball and FIG. 5(b) illustrating the state of a process on a near side of the eyeball.
Figure 5:
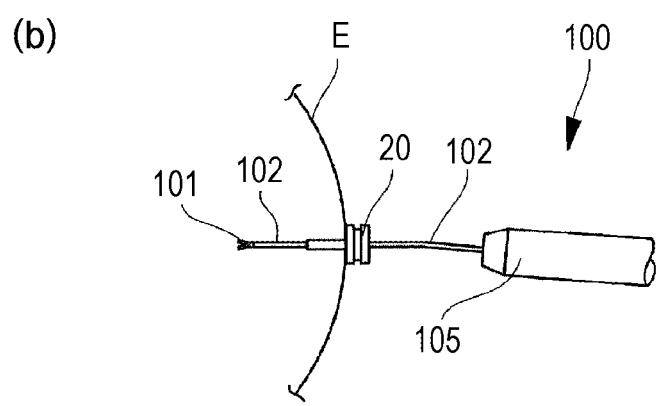
Figure 6:
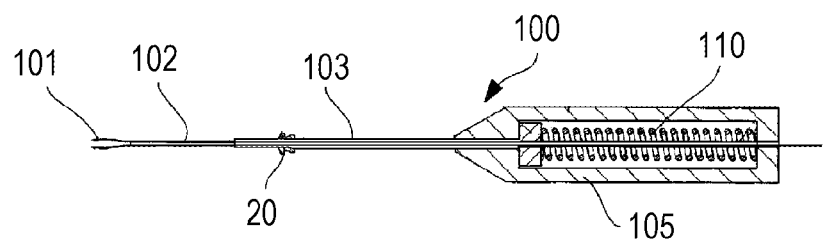
FIG. 6 illustrates a cross-sectional view of a typical surgical probe having a reinforcement sleeve.

The tip end reinforcement pipe 13d described herein may be longer than the body portion of the reinforcement sleeve 13. FIG. 4 illustrates an example in a case where the tip end reinforcement pipe 13d is long. In this case, a structure is made, in which the tip end reinforcement pipe 13d of the reinforcement sleeve 13 has a smaller outer diameter than the outer diameter of the body portion of the reinforcement sleeve 13 and penetrates the through-hole of the body portion 15.

The body portion of the reinforcement sleeve 13 may be only a portion corresponding to a length including the slide knobs 13a and the claw portions 13c, or the tip end reinforcement pipe 13d may form the entirety of the remaining portion to form the reinforcement sleeve 13. In this case, it may be configured such that the tip end reinforcement pipe 13d does not have the slit 13b. For connection between the body portion of the reinforcement sleeve 13 and the tip end reinforcement pipe 13d, an appropriate method such as press-fitting, swaging, or bonding can be used. Note that in the present example, the tip end reinforcement pipe 13d is long, and therefore, rattling of the reinforcement sleeve 13 and the pipe 12 can be further reduced.

With the above-described ophthalmic surgical instrument including the reinforcement sleeve, there are advantageous effects that the reinforcement sleeve slidably covers the pipe so that curving of the pipe can be prevented and moderately contacts the body portion of the ophthalmic surgical instrument so that the reinforcement sleeve can receive friction resistance upon sliding and can be pulled out by the required length to cover the pipe. Moreover, the reinforcement sleeve and the pipe form the mechanisms sliding independently of each other so that the degree of freedom in design of the slide mechanism can be improved.

LIST OF REFERENCE SIGNS

10 vitreous forceps (ophthalmic surgical instrument)
11 working portion
12 pipe
13 reinforcement sleeve
13a slide knob
13b slit
13c claw portion
13d tip end reinforcement pipe
15 body portion
16 operating portion
17 movement member
20 cannula

What is claimed is:

1. An ophthalmic surgical instrument working in an eyeball, comprising:
    a body portion including a through-hole;
    a reinforcement sleeve contacting an inner surface of the through-hole of the body portion, the reinforcement sleeve having a slide knob;
    a pipe passing through an inside of the reinforcement sleeve and having a working portion protruding from a tip end; and
    a movement member connected to the pipe and sliding in an axial direction of the ophthalmic surgical instrument to slide the pipe,
    wherein a first slide mechanism allowing the reinforcement sleeve to slide in the axial direction of the ophthalmic surgical instrument coupled with the slide knob, and a second slide mechanism allowing the pipe to slide in the axial direction of the ophthalmic surgical instrument are provided,
    the first and second slide mechanisms are an independent slide mechanism not influenced by the other slide mechanism, and
    in the second slide mechanism, the movement member is connected to the pipe, and the movement member is connected to an operation portion through a plate spring, and,
    a connection portion of the movement member and the pipe is closer, in the axial direction of the ophthalmic surgical instrument, to a base of the ophthalmic surgical instrument than a connection portion of the operation portion and the plate spring is.

2. The ophthalmic surgical instrument according to claim 1, wherein the reinforcement sleeve includes a slit in the axial direction.

3. The ophthalmic surgical instrument according to claim 1, wherein
    the reinforcement sleeve includes a claw portion at a back end position, and
    the claw portion contacts an inside of the body portion.

4. The ophthalmic surgical instrument according to claim 1, wherein
    a metal tip end reinforcement pipe is provided on a tip end side of the reinforcement sleeve, and the pipe penetrates the tip end reinforcement pipe.

5. The ophthalmic surgical instrument according to claim 1, wherein
    the body portion further includes a slit extending along the axial direction of the ophthalmic surgical instrument and communicating with the through-hole of the body portion and
    the slide knob is disposed in the slit of the body portion.

\* \* \* \* \*